United States Patent
Golemis et al.

[11] Patent Number: 6,124,434
[45] Date of Patent: Sep. 26, 2000

[54] SIGNAL MEDIATOR PROTEIN THAT INDUCES CELLULAR MORPHOLOGICAL ALTERATIONS

[75] Inventors: Erica A. Golemis, Oreland; Susan F. Law, Unionville; Joanne Estojak, Jenkintown, all of Pa.

[73] Assignee: Fox Chase Cancer Center, Philadelphia, Pa.

[21] Appl. No.: 09/196,466

[22] Filed: Nov. 19, 1998

Related U.S. Application Data

[60] Continuation of application No. 08/968,633, Nov. 12, 1997, which is a division of application No. 08/491,357, Jun. 30, 1995, Pat. No. 5,716,782.

[51] Int. Cl.⁷ .............. C07K 1/00; C12Q 1/68; C12P 21/06; C07H 21/00
[52] U.S. Cl. ............. 530/350; 435/69.1; 435/6; 536/23.1
[58] Field of Search .......... 435/6, 320.1, 252.3, 435/69.1; 530/350; 536/23.1

[56] References Cited

U.S. PATENT DOCUMENTS 5,716,782  2/1998  Golemis et al. ............... 435/6

FOREIGN PATENT DOCUMENTS

WO97/02362  1/1997  WIPO.

*Primary Examiner*—Karen Cochrane Carlson
*Assistant Examiner*—Devesh Srivastava
*Attorney, Agent, or Firm*—Dann, Dorfman, Herrell and Skillman

[57] ABSTRACT

An isolated nucleic acid molecule is provided which encodes a mammalian signal mediator protein involved in regulation of cellular morphological alterations. The encoded protein comprises an amino-terminal SH3 domain, an Internal domain containing several SH2 binding motifs, and a carboxy-terminal effector domain that can induce pseudohyphal budding in yeast. The invention also provides the novel signal mediator protein, and antibodies thereto. These biological molecules are useful as research tools and as diagnostic and therapeutic agents for the identification, detection and regulation of complex signaling events leading to morphological, potentially neoplastic, cellular changes.

5 Claims, 6 Drawing Sheets

```
accccacgctaccgaaATGAAGTATAAGAATCTTATGGCAAGGGCCTTATATGACAAT
                 M  K  Y  K  N  L  M  A  R  A  L  Y  D  N
GTCCCAGAGTGTGCCGAGGAACTGGCCTTTCGCAAGGGAGACATCCTGACCGTCATAGAG
 V  P  E  C  A  E  E  L  A  F  R  K  G  D  I  L  T  V  I  E
CAGAACACAGGGGGACTGGAAGGATGGTGGCTGTGTCGTTACACGGTCGGCAAGGCATT
 Q  N  T  G  G  L  E  G  W  W  L  C  S  L  H  G  R  Q  G  I
GTCCCAGGCAACCGGGTGAAGCTTCTGATTGGCCCCATGCAGGAGACTGCCTCCAGTCAC
 V  P  G  N  R  V  K  L  L  I  G  P  M  Q  E  T  A  S  S  H
GAGCAGCCTGCCTCTGGACTGATGCAGCAGACCTTTGGCCAACAGAAGCTCTATCAAGTG
 E  Q  P  A  S  G  L  M  Q  Q  T  F  G  Q  Q  K  L  Y  Q  V
CCAAACCCACAGGCTGCTCCCCGAGACACTATCTACCAAGTGCCACCTTCCTACCAAAAT
 P  N  P  Q  A  A  P  R  D  T  I  Y  Q  V  P  P  S  Y  Q  N
CAGGGAATTTACCAAGTCCCCACTGGCCACGGCACCCAAGAACAAGAGGTATATCAGGTG
 Q  G  I  Y  Q  V  P  T  G  H  G  T  Q  E  Q  E  V  Y  Q  V
CCACCATCAGTGCAGAGAAGCATTGGGGGAACCAGTGGGCCCCACGTGGGTAAAAAGGTG
 P  P  S  V  Q  R  S  I  G  G  T  S  G  P  H  V  G  K  K  V
ATAACCCCCGTGAGGACAGGCCATGGCTACGTATACGAGTACCCATCCAGATACCAAAAG
 I  T  P  V  R  T  G  H  G  Y  V  Y  E  Y  P  S  R  Y  Q  K
GATGTCTATGATATCCCTCCTTCTCATACCACTCAAGGGGTATACGACATCCCTCCCTCA
 D  V  Y  D  I  P  P  S  H  T  T  Q  G  V  Y  D  I  P  P  S
TCAGCAAAAGGCCCTGTGTTTTCAGTTCCAGTGGGAGAGATAAAACCTCAAGGGGTGTAT
 S  A  K  G  P  V  F  S  V  P  V  G  E  I  K  P  Q  G  V  Y
GACATCCCGCCTACAAAAGGGGTATATGCCATTCCGCCCTCTGCTTGCCGGGATGAAGCA
 D  I  P  P  T  K  G  V  Y  A  I  P  P  S  A  C  R  D  E  A
GGGCTTAGGGAAAAAGACTATGACTTCCCCCCTCCCATGAGACAAGCTGGAAGGCCGGAC
 G  L  R  E  K  D  Y  D  F  P  P  P  M  R  Q  A  G  R  P  D
CTCAGACCGGAGGGGGTTTATGACATTCCTCCAACCTGCACCAAGCCAGCAGGGAAGGAC
 L  R  P  E  G  V  Y  D  I  P  P  T  C  T  K  P  A  G  K  D
CTTCATGTAAAATACAACTGTGACATTCCAGGAGCTGCAGAACCGGTGGCTCGAAGGCAC
```

```
accccacgctaccgaaATGAAGTATAAGAATCTTATGGCAAGGGCCTTATATGACAAT
                 M  K  Y  K  N  L  M  A  R  A  L  Y  D  N
GTCCCAGAGTGTGCCGAGGAACTGGCCTTTCGCAAGGGAGACATCCTGACCGTCATAGAG
 V  P  E  C  A  E  E  L  A  F  R  K  G  D  I  L  T  V  I  E
CAGAACACAGGGGGACTGGAAGGATGGTGGCTGTGCTCGTTACACGGTCGGCAAGGCATT
 Q  N  T  G  G  L  E  G  W  W  L  C  S  L  H  G  R  Q  G  I
GTCCCAGGCAACCGGGTGAAGCTTCTGATTGGCCCCATGCAGGAGACTGCCTCCAGTCAC
 V  P  G  N  R  V  K  L  L  I  G  P  M  Q  E  T  A  S  S  H
GAGCAGCCTGCCTCTGGACTGATGCAGCAGACCTTTGGCCAACAGAAGCTCTATCAAGTG
 E  Q  P  A  S  G  L  M  Q  Q  T  F  G  Q  Q  K  L  Y  Q  V
CCAAACCCACAGGCTGCTCCCCGAGACACTATCTACCAAGTGCCACCTTCCTACCAAAAT
 P  N  P  Q  A  A  P  R  D  T  I  Y  Q  V  P  P  S  Y  Q  N
CAGGGAATTTACCAAGTCCCCACTGGCCACGGCACCCAAGAACAAGAGGTATATCAGGTG
 Q  G  I  Y  Q  V  P  T  G  H  G  T  Q  E  Q  E  V  Y  Q  V
CCACCATCAGTGCAGAGAAGCATTGGGGGAACCAGTGGGCCCCACGTGGGTAAAAAGGTG
 P  P  S  V  Q  R  S  I  G  G  T  S  G  P  H  V  G  K  K  V
ATAACCCCCGTGAGGACAGGCCATGGCTACGTATACGAGTACCCATCCAGATACCAAAAG
 I  T  P  V  R  T  G  H  G  Y  V  Y  E  Y  P  S  R  Y  Q  K
GATGTCTATGATATCCCTCCTTCTCATACCACTCAAGGGGTATACGACATCCCTCCCTCA
 D  V  Y  D  I  P  P  S  H  T  T  Q  G  V  Y  D  I  P  P  S
TCAGCAAAAGGCCCTGTGTTTTCAGTTCCAGTGGGAGAGATAAAACCTCAAGGGGTGTAT
 S  A  K  G  P  V  F  S  V  P  V  G  E  I  K  P  Q  G  V  Y
GACATCCCGCCTACAAAAGGGGTATATGCCATTCCGCCCTCTGCTTGCCGGGATGAAGCA
 D  I  P  P  T  K  G  V  Y  A  I  P  P  S  A  C  R  D  E  A
GGGCTTAGGGAAAAAGACTATGACTTCCCCCCTCCCATGAGACAAGCTGGAAGGCCGGAC
 G  L  R  E  K  D  Y  D  F  P  P  P  M  R  Q  A  G  R  P  D
CTCAGACCGGAGGGGGTTTATGACATTCCTCCAACCTGCACCAAGCCAGCAGGGAAGGAC
 L  R  P  E  G  V  Y  D  I  P  P  T  C  T  K  P  A  G  K  D
CTTCATGTAAAATACAACTGTGACATTCCAGGAGCTGCAGAACCGGTGGCTCGAAGGCAC
```

Figure 1A

```
       L  H  V  K  Y  N  C  D  I  P  G  A  A  E  P  V  A  R  R  H
CAGAGCCTGTCCCCGAATCACCCACCCCCGCAACTCGGACAGTCAGTGGGCTCTCAGAAC
 Q  S  L  S  P  N  H  P  P  P  Q  L  G  Q  S  V  G  S  Q  N
GACGCATATGATGTCCCCCGAGGCGTTCAGTTTCTTGAGCCACCAGCAGAAACCAGTGAG
 D  A  Y  D  V  P  R  G  V  Q  F  L  E  P  P  A  E  T  S  E
AAAGCAAACCCCCAGGAAAGGGATGGTGTTTATGATGTCCCTCTGCATAACCCGCCAGAT
 K  A  N  P  Q  E  R  D  G  V  Y  D  V  P  L  H  N  P  P  D
GCTAAAGGCTCTCGGGACTTGGTGGATGGGATCAACCGATTGTCTTTCTCCAGTACAGGC
 A  K  G  S  R  D  L  V  D  G  I  N  R  L  S  F  S  S  T  G
AGCACCCGGAGTAACATGTCCACGTCTTCCACCTCCTCCAAGGAGTCCTCACTGTCAGCC
 S  T  R  S  N  M  S  T  S  S  T  S  S  K  E  S  S  L  S  A
TCCCCAGCTCAGGACAAAAGGCTCTTCCTGGATCCAGACACAGCTATTGAGAGACTTCAG
 S  P  A  Q  D  K  R  L  F  L  D  P  D  T  A  I  E  R  L  Q
CGGCTCCAGCAGGCCCTTGAGATGGGTGTCTCCAGCCTAATGGCACTGGTCACTACCGAC
 R  L  Q  Q  A  L  E  M  G  V  S  S  L  M  A  L  V  T  T  D
TGGCGGTGTTACGGATATATGGAAAGACACATCAATGAAATACGCACAGCAGTGGACAAG
 W  R  C  Y  G  Y  M  E  R  H  I  N  E  I  R  T  A  V  D  K
GTGGAGCTGTTCCTGAAGGAGTACCTCCACTTTGTCAAGGGAGCTGTTGCAAATGCTGCC
 V  E  L  F  L  K  E  Y  L  H  F  V  K  G  A  V  A  N  A  A
TGCCTCCCGGAACTCATCCTCCACAACAAGATGAAGCGGGAGCTGCAACGAGTCGAAGAC
 C  L  P  E  L  I  L  H  N  K  M  K  R  E  L  Q  R  V  E  D
TCCCACCAGATCCTGAGTCAAACCAGCCATGACTTAAATGAGTGCAGCTGGTCCCTGAAT
 S  H  Q  I  L  S  Q  T  S  H  D  L  N  E  C  S  W  S  L  N
ATCTTGGCCATCAACAAGCCCCAGAACAAGTGTGACGATCTGGACCGGTTTGTGATGGTG
 I  L  A  I  N  K  P  Q  N  K  C  D  D  L  D  R  F  V  M  V
GCAAAGACGGTGCCCGATGACGCCAAGCAGCTCACCACAACCATCAACACCAACGCAGAG
 A  K  T  V  P  D  D  A  K  Q  L  T  T  T  I  N  T  N  A  E
GCCCTCTTCAGACCCGGCCCTGGCAGCTTGCATCTGAAGAATGGGCCGGAGAGCATCATG
 A  L  F  R  P  G  P  G  S  L  H  L  K  N  G  P  E  S  I  M
```

Figure 1B

```
AACTCAACGGAGTACCCACACGGTGGCTCCCAGGGACAGCTGCTGCATCCTGGTGACCAC
 N   S   T   E   Y   P   H   G   G   S   Q   G   Q   L   L   H   P   G   D   H

AAGGCCCAGGCCCACAACAAGGCACTGCCCCCAGGCCTGAGCAAGGAGCAGGCCCCTGAC
 K   A   Q   A   H   N   K   A   L   P   P   G   L   S   K   E   Q   A   P   D

TGTAGCAGCAGTGATGGTTCTGAGAGGAGCTGGATGGATGACTACGATTACGTCCACCTA
 C   S   S   S   D   G   S   E   R   S   W   M   D   D   Y   D   Y   V   H   L

CAGGGTAAGGAGGAGTTTGAGAGGCAACAGAAAGAGCTATTGGAAAAAGAGAATATCATG
 Q   G   K   E   E   F   E   R   Q   Q   K   E   L   L   E   K   E   N   I   M

AAACAGAACAAGATGCAGCTGGAACATCATCAGCTGAGCCAGTTCCAGCTGTTGGAACAA
 K   Q   N   K   M   Q   L   E   H   H   Q   L   S   Q   F   Q   L   L   E   Q

GAGATTACAAAGCCCGTGGAGAATGACATCTCGAAGTGGAAGCCCTCTCAGAGCCTACCC
 E   I   T   K   P   V   E   N   D   I   S   K   W   K   P   S   Q   S   L   P

ACCACAAACAGTGGCGTGAGTGCTCAGGATCGGCAGTTGCTGTGCTTCTACTATGACCAA
 T   T   N   S   G   V   S   A   Q   D   R   Q   L   L   C   F   Y   Y   D   Q

TGTGAGACCCATTTCATTTCCCTTCTCAACGCCATTGACGCACTCTTCAGTTGTGTCAGC
 C   E   T   H   F   I   S   L   L   N   A   I   D   A   L   F   S   C   V   S

TCAGCCCAGCCCCCGCGAATCTTCGTGGCACACAGCAAGTTTGTCATCCTCAGTGCACAC
 S   A   Q   P   P   R   I   F   V   A   H   S   K   F   V   I   L   S   A   H

AAACTGGTGTTCATTGGAGACACGCTGACACGGCAGGTGACTGCCCAGGACATTCGCAAC
 K   L   V   F   I   G   D   T   L   T   R   Q   V   T   A   Q   D   I   R   N

AAAGTCATGAACTCCAGCAACCAGCTCTGCGAGCAGCTCAAGACTATAGTCATGGCAACC
 K   V   M   N   S   S   N   Q   L   C   E   Q   L   K   T   I   V   M   A   T

AAGATGGCCGCCCTCCATTACCCCAGCACCACGGCCCTGCAGGAAATGGTGCACCAAGTG
 K   M   A   A   L   H   Y   P   S   T   T   A   L   Q   E   M   V   H   Q   V

ACAGACCTTTCTAGAAATGCCCAGCTGTTCAAGCGCTCTTTGCTGGAGATGGCAACGTTC
 T   D   L   S   R   N   A   Q   L   F   K   R   S   L   L   E   M   A   T   F

TGAGAAGAAAAAAAGAGGAAGGGGACTGCGTTAACGGTTACTAAGGAAAACTGGAAATA
 *

CTGTCTGGTTTTTGTAAATGTTATCTATTTTTGTAGATAATTTTATATAAAAATGAAATA
TTTTAACATTTTATGGGTCAGACAACTTTCAGAAATTCAGGGAGCTGGAGAGGGAAATCT
TTTTTTCCCCCCTGAGTXGTTCTTATGTATACACAGAAGTATCTGAGACATAAACTGTAC
AGAAAACTTGTCCACGTCCTTTTGTATGCCCATGTATTCATGTTTTTGTTTGTAGATGTT
```

Figure 1C

```
TGTCTGATGCATTTCATTAAAAAAAAAACCATGAATTACGAAGCACCTTAGTAAGCACCT
TCTAATGCTGCATTTTTTTTGTTGTTGTTAAAAACATCCAGCTGGTTATAATATTGTTCT
CCACGTCCTTGTGATGATTCTGAGCCTGGCACTGGGAATCTGGGAAGCATAGTTTATTTG
CAAGTGTTCACCTTCCAAATCATGAGGCATAGCATGACTTATTCTTGTTTTGAAAACTCT
TTTCAAAACTGACCATCTTAAACACATGATGGCCAAGTGCCACAAAGCCCTCTTGCGGAG
ACATTTACGAATATATATGTGGATCCAAGTCTCGATAGTTAGGCGTTGGAGGGAAGAGAG
ACCAGAGAGTTTAGAGGCCAGGACCACAGTTAGGATTGGGTTGTTTCAATACTGAGAGAC
AGCTACAATAAAAGGAGAGCAATTGCCTCCCTGGGGCTGTTCAATCTTCTGCATTTGTGA
GTGGTTCAGTCATGAGGTTTTCCAAAAGATGTTTTTAGAGTTGTAAAAACCATATTTGCA
GCAAAGATTTACAAAGGCGTATCAGACTATGATTGTTCACCAAAATAGGGGAATGGTTTG
ATCCGCCAGTTGCAAGTAGAGGCCTTTCTGACTCTTAATATTCACTTTGGTGCTACTACC
CCCATTACCTGAGGAACTGGCCAGGTCCTTGATCATGGAACTATAGAGCTACCAGACATA
TCCTGCTCTCTAAGGGAATTTATTGCTATCTTGCACCTTCTTTAAAACTCAAAAAACATA
TGCAGACCTGACACTCAAGAGTGGCTAGCTACACAGAGTCCATCTAATTTTTGCAACTTC
CCCCCCCGAATTC
```

```
HEF1      LSQFQLLEQEITKPVENDISKWKPSQSL.PTTNSGVSAQDRQLLCFYYDQCETHFISL
MEF1      LSQFQLLEQEITKPVENDISKWKPSQSL.PTTNNSVSAQDRQLLCFYYDQCETHFISL
p130cas   LKQFERLEQEVSRPIDHDLANWTPAQPLVPGRTGGLGPSDRQLLLFYLEQCEANLTTL HEF1      LNAIDALFSCVSSAQPPRIFV
MEF1      LNAIDALFSCVSSAQPPRIFV
p130cas   TDAVDAFFTAVATNQPPKIFV
```

Figure 3

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
       (A) LENGTH: 3672 base pairs
       (B) TYPE: nucleic acid
       (C) STRANDEDNESS: single
       (D) TOPOLOGY: Not Relevant (ii) MOLECULE TYPE: DNA (genomic)

(iii) HYPOTHETICAL: NO (iv) ANTI-SENSE: NO (xi) SEQUENCE DESCRIPTION: SEQ ID NO:1:

```
ACCCCCACGC TACCGAAATG AAGTATAAGA ATCTTATGGC AAGGGCCTTA TATGACAATG      60
TCCCAGAGTG TGCCGAGGAA CTGGCCTTTC GCAAGGGAGA CATCCTGACC GTCATAGAGC     120
AGAACACAGG GGGACTGGAA GGATGGTGGC TGTGCTCGTT ACACGGTCGG CAAGGCATTG     180
TCCCAGGCAA CCGGGTGAAG CTTCTGATTG GCCCCATGCA GGAGACTGCC TCCAGTCACG     240
AGCAGCCTGC CTCTGGACTG ATGCAGCAGA CCTTTGGCCA ACAGAAGCTC TATCAAGTGC     300
CAAACCCACA GGCTGCTCCC CGAGACACTA TCTACCAAGT GCCACCTTCC TACCAAAATC     360
AGGGAATTTA CCAAGTCCCC ACTGGCCACG GCACCCAAGA ACAAGAGGTA TATCAGGTGC     420
CACCATCAGT GCAGAGAAGC ATTGGGGGAA CCAGTGGGCC CCACGTGGGT AAAAAGGTGA     480
TAACCCCCGT GAGGACAGGC CATGGCTACG TATACGAGTA CCCATCCAGA TACCAAAAGG     540
ATGTCTATGA TATCCCTCCT TCTCATACCA CTCAAGGGGT ATACGACATC CCTCCCTCAT     600
CAGCAAAAGG CCCTGTGTTT TCAGTTCCAG TGGGAGAGAT AAAACCTCAA GGGGTGTATG     660
ACATCCCGCC TACAAAAGGG GTATATGCCA TTCCGCCCTC TGCTTGCCGG GATGAAGCAG     720
GGCTTAGGGA AAAAGACTAT GACTTCCCCC CTCCCATGAG ACAAGCTGGA AGGCCGGACC     780
TCAGACCGGA GGGGGTTTAT GACATTCCTC CAACCTGCAC CAAGCCAGCA GGGAAGGACC     840
TTCATGTAAA ATACAACTGT GACATTCCAG GAGCTGCAGA ACCGGTGGCT CGAAGGCACC     900
AGAGCCTGTC CCCGAATCAC CCACCCCCGC AACTCGGACA GTCAGTGGGC CTCAGAACGA     960
ACGCATATGA TGTCCCCCGA GGCGTTCAGT TTCTTGAGCC ACCAGCAGAA ACCAGTGAGA    1020
AAGCAAACCC CCAGGAAAGG GATGGTGTTT ATGATGTCCC TCTGCATAAC CCGCCAGATG    1080
CTAAAGGCTC TCGGGACTTG GTGGATGGGA TCAACCGATT GTCTTTCTCC AGTACAGGCA    1140
GCACCCGGAG TAACATGTCC ACGTCTTCCA CCTCCTCCAA GGAGTCCTCA CTGTCAGCCT    1200
CCCCAGCTCA GGACAAAAGG CTCTTCCTGG ATCCAGACAC AGCTATTGAG AGACTTCAGC    1260
GGCTCCAGCA GGCCCTTGAG ATGGGTGTCT CCAGCCTAAT GGCACTGGTC ACTACCGACT    1320
GGCGGTGTTA CGGATATATG GAAAGACACA TCAATGAAAT ACGCACAGCA GTGGACAAGG    1380
TGGAGCTGTT CCTGAAGGAG TACCTCCACT TTGTCAAGGG AGCTGTTGCA AATGCTGCCT    1440
GCCTCCCGGA ACTCATCCTC CACAACAAGA TGAAGCGGGA GCTGCAACGA GTCGAAGACT    1500
CCCACCAGAT CCTGAGTCAA ACCAGCCATG ACTTAAATGA GTGCAGCTGG TCCCTGAATA    1560
TCTTGGCCAT CAACAAGCCC CAGAACAAGT GTGACGATCT GGACCGGTTT GTGATGGTGG    1620
CAAAGACGGT GCCCGATGAC GCCAAGCAGC TCACCACAAC CATCAACACC AACGCAGAGG    1680
```

```
CCCTCTTCAG ACCCGGCCCT GGCAGCTTGC ATCTGAAGAA TGGGCCGGAG AGCATCATGA    1740

ACTCAACGGA GTACCCACAC GGTGGCTCCC AGGGACAGCT GCTGCATCCT GGTGACCACA    1800

AGGCCCAGGC CCACAACAAG GCACTGCCCC CAGGCCTGAG CAAGGAGCAG GCCCCTGACT    1860

GTAGCAGCAG TGATGGTTCT GAGAGGAGCT GGATGGATGA CTACGATTAC GTCCACCTAC    1920

AGGGTAAGGA GGAGTTTGAG AGGCAACAGA AAGAGCTATT GGAAAAAGAG AATATCATGA    1980

AACAGAACAA GATGCAGCTG GAACATCATC AGCTGAGCCA GTTCCAGCTG TTGGAACAAG    2040

AGATTACAAA GCCCGTGGAG AATGACATCT CGAAGTGGAA GCCCTCTCAG AGCCTACCCA    2100

CCACAAACAG TGGCGTGAGT GCTCAGGATC GGCAGTTGCT GTGCTTCTAC TATGACCAAT    2160

GTGAGACCCA TTTCATTTCC CTTCTCAACG CCATTGACGC ACTCTTCAGT TGTGTCAGCT    2220

CAGCCCAGCC CCCGCGAATC TTCGTGGCAC ACAGCAAGTT TGTCATCCTC AGTGCACACA    2280

AACTGGTGTT CATTGGAGAC ACGCTGACAC GGCAGGTGAC TGCCCAGGAC ATTCGCAACA    2340

AAGTCATGAA CTCCAGCAAC CAGCTCTGCG AGCAGCTCAA GACTATAGTC ATGGCAACCA    2400

AGATGGCCGC CCTCCATTAC CCCAGCACCA CGGCCCTGCA GGAAATGGTG CACCAAGTGA    2460

CAGACCTTTC TAGAAATGCC CAGCTGTTCA AGCGCTCTTT GCTGGAGATG CAACGTTCT     2520

GAGAAGAAAA AAAAGAGGAA GGGGACTGCG TTAACGGTTA CTAAGGAAAA CTGGAAATAC    2580

TGTCTGGTTT TTGTAAATGT TATCTATTTT TGTAGATAAT TTTATATAAA AATGAAATAT    2640

TTTAACATTT TATGGGTCAG ACAACTTTCA GAAATTCAGG GAGCTGGAGA GGGAAATCTT    2700

TTTTTCCCCC CTGAGTNGTT CTTATGTATA CACAGAAGTA TCTGAGACAT AAACTGTACA    2760

GAAAACTTGT CCACGTCCTT TTGTATGCCC ATGTATTCAT GTTTTTGTTT GTAGATGTTT    2820

GTCTGATGCA TTTCATTAAA AAAAAAACCA TGAATTACGA AGCACCTTAG TAAGCACCTT    2880

CTAATGCTGC ATTTTTTTTG TTGTTGTTAA AAACATCCAG CTGGTTATAA TATTGTTCTC    2940

CACGTCCTTG TGATGATTCT GAGCCTGGCA CTGGGAATCT GGGAAGCATA GTTTATTTGC    3000

AAGTGTTCAC CTTCCAAATC ATGAGGCATA GCATGACTTA TTCTTGTTTT GAAAACTCTT    3060

TTCAAAACTG ACCATCTTAA ACACATGATG GCCAAGTGCC ACAAAGCCCT CTTGCGGAGA    3120

CATTTACGAA TATATATGTG GATCCAAGTC TCGATAGTTA GGCGTTGGAG GGAAGAGAGA    3180

CCAGAGAGTT TAGAGGCCAG GACCACAGTT AGGATTGGGT TGTTTCAATA CTGAGAGACA    3240

GCTACAATAA AAGGAGAGCA ATTGCCTCCC TGGGGCTGTT CAATCTTCTG CATTTGTGAG    3300

TGGTTCAGTC ATGAGGTTTT CCAAAAGATG TTTTTAGAGT TGTAAAAACC ATATTTGCAG    3360

CAAAGATTTA CAAAGGCGTA TCAGACTATG ATTGTTCACC AAAATAGGGG AATGGTTTGA    3420

TCCGCCAGTT GCAAGTAGAG GCCTTTCTGA CTCTTAATAT TCACTTTGGT GCTACTACCC    3480

CCATTACCTG AGGAACTGGC CAGGTCCTTG ATCATGGAAC TATAGAGCTA CCAGACATAT    3540

CCTGCTCTCT AAGGGAATTT ATTGCTATCT TGCACCTTCT TTAAAACTCA AAAACATAT    3600

GCAGACCTGA CACTCAAGAG TGGCTAGCTA CACAGAGTCC ATCTAATTTT TGCAACTTCC    3660

CCCCCCGAAT TC                                                       3672
```

(2) INFORMATION FOR SEQ ID NO:2:

(i) SEQUENCE CHARACTERISTICS:
        (A) LENGTH: 834 amino acids
        (B) TYPE: amino acid
        (C) STRANDEDNESS: Not Relevant
        (D) TOPOLOGY: Not Relevant (ii) MOLECULE TYPE: protein (iii) HYPOTHETICAL: NO (iv) ANTI-SENSE: NO (xi) SEQUENCE DESCRIPTION: SEQ ID NO:2:

```
Met Lys Tyr Lys Asn Leu Met Ala Arg Ala Leu Tyr Asp Asn Val Pro
 1               5                  10                  15

Glu Cys Ala Glu Glu Leu Ala Phe Arg Lys Gly Asp Ile Leu Thr Val
                20                  25                  30

Ile Glu Gln Asn Thr Gly Gly Leu Glu Gly Trp Trp Leu Cys Ser Leu
            35                  40                  45

His Gly Arg Gln Gly Ile Val Pro Gly Asn Arg Val Lys Leu Leu Ile
        50                  55                  60

Gly Pro Met Gln Glu Thr Ala Ser Ser His Glu Gln Pro Ala Ser Gly
 65                  70                  75                  80

Leu Met Gln Gln Thr Phe Gly Gln Gln Lys Leu Tyr Gln Val Pro Asn
                85                  90                  95

Pro Gln Ala Ala Pro Arg Asp Thr Ile Tyr Gln Val Pro Pro Ser Tyr
               100                 105                 110

Gln Asn Gln Gly Ile Tyr Gln Val Pro Thr Gly His Gly Thr Gln Glu
            115                 120                 125

Gln Glu Val Tyr Gln Val Pro Pro Ser Val Gln Arg Ser Ile Gly Gly
        130                 135                 140

Thr Ser Gly Pro His Val Gly Lys Lys Val Ile Thr Pro Val Arg Thr
145                 150                 155                 160

Gly His Gly Tyr Val Tyr Glu Tyr Pro Ser Arg Tyr Gln Lys Asp Val
                165                 170                 175

Tyr Asp Ile Pro Pro Ser His Thr Thr Gln Gly Val Tyr Asp Ile Pro
            180                 185                 190

Pro Ser Ala Lys Gly Pro Val Phe Ser Val Pro Val Gly Glu Ile
        195                 200                 205

Lys Pro Gln Gly Val Tyr Asp Ile Pro Pro Thr Lys Gly Val Tyr Ala
210                 215                 220

Ile Pro Pro Ser Ala Cys Arg Asp Glu Ala Gly Leu Arg Glu Lys Asp
225                 230                 235                 240

Tyr Asp Phe Pro Pro Pro Met Arg Gln Ala Gly Arg Pro Asp Leu Arg
                245                 250                 255

Pro Glu Gly Val Tyr Asp Ile Pro Pro Thr Cys Thr Lys Pro Ala Gly
            260                 265                 270

Lys Asp Leu His Val Lys Tyr Asn Cys Asp Ile Pro Gly Ala Ala Glu
        275                 280                 285

Pro Val Ala Arg Arg His Gln Ser Leu Ser Pro Asn His Pro Pro Pro
290                 295                 300

Gln Leu Gly Gln Ser Val Gly Ser Gln Asn Asp Ala Tyr Asp Val Pro
305                 310                 315                 320

Arg Gly Val Gln Phe Leu Glu Pro Pro Ala Glu Thr Ser Glu Lys Ala
                325                 330                 335

Asn Pro Gln Glu Arg Asp Gly Val Tyr Asp Val Pro Leu His Asn Pro
            340                 345                 350

Pro Asp Ala Lys Gly Ser Arg Asp Leu Val Asp Gly Ile Asn Arg Leu
        355                 360                 365

Ser Phe Ser Ser Thr Gly Ser Thr Arg Ser Asn Met Ser Thr Ser Ser
370                 375                 380
```

```
Thr Ser Ser Lys Glu Ser Ser Leu Ser Ala Ser Pro Ala Gln Asp Lys
385                 390                 395                 400

Arg Leu Phe Leu Asp Pro Asp Thr Ala Ile Glu Arg Leu Gln Arg Leu
                405                 410                 415

Gln Gln Ala Leu Glu Met Gly Val Ser Ser Leu Met Ala Leu Val Thr
            420                 425                 430

Thr Asp Trp Arg Cys Tyr Gly Tyr Met Glu Arg His Ile Asn Glu Ile
        435                 440                 445

Arg Thr Ala Val Asp Lys Val Glu Leu Phe Leu Lys Glu Tyr Leu His
    450                 455                 460

Phe Val Lys Gly Ala Val Ala Asn Ala Ala Cys Leu Pro Glu Leu Ile
465                 470                 475                 480

Leu His Asn Lys Met Lys Arg Glu Leu Gln Arg Val Glu Asp Ser His
                485                 490                 495

Gln Ile Leu Ser Gln Thr Ser His Asp Leu Asn Glu Cys Ser Trp Ser
            500                 505                 510

Leu Asn Ile Leu Ala Ile Asn Lys Pro Gln Asn Lys Cys Asp Asp Leu
        515                 520                 525

Asp Arg Phe Val Met Val Ala Lys Thr Val Pro Asp Asp Ala Lys Gln
    530                 535                 540

Leu Thr Thr Thr Ile Asn Thr Asn Ala Glu Ala Leu Phe Arg Pro Gly
545                 550                 555                 560

Pro Gly Ser Leu His Leu Lys Asn Gly Pro Glu Ser Ile Met Asn Ser
                565                 570                 575

Thr Glu Tyr Pro His Gly Gly Ser Gln Gly Leu Leu His Pro Gly
            580                 585                 590

Asp His Lys Ala Gln Ala His Asn Lys Ala Leu Pro Pro Gly Leu Ser
        595                 600                 605

Lys Glu Gln Ala Pro Asp Cys Ser Ser Ser Asp Gly Ser Glu Arg Ser
    610                 615                 620

Trp Met Asp Asp Tyr Asp Tyr Val His Leu Gln Gly Lys Glu Glu Phe
625                 630                 635                 640

Glu Arg Gln Gln Lys Glu Leu Leu Glu Lys Glu Asn Ile Met Lys Gln
                645                 650                 655

Asn Lys Met Gln Leu Glu His His Gln Leu Ser Gln Phe Gln Leu Leu
            660                 665                 670

Glu Gln Glu Ile Thr Lys Pro Val Glu Asn Asp Ile Ser Lys Trp Lys
        675                 680                 685

Pro Ser Gln Ser Leu Pro Thr Thr Asn Ser Gly Val Ser Ala Gln Asp
    690                 695                 700

Arg Gln Leu Leu Cys Phe Tyr Tyr Asp Gln Cys Glu Thr His Phe Ile
705                 710                 715                 720

Ser Leu Leu Asn Ala Ile Asp Ala Leu Phe Ser Cys Val Ser Ser Ala
                725                 730                 735

Gln Pro Pro Arg Ile Phe Val Ala His Ser Lys Phe Val Ile Leu Ser
            740                 745                 750

Ala His Lys Leu Val Phe Ile Gly Asp Thr Leu Thr Arg Gln Val Thr
        755                 760                 765

Ala Gln Asp Ile Arg Asn Lys Val Met Asn Ser Ser Asn Gln Leu Cys
    770                 775                 780

Glu Gln Leu Lys Thr Ile Val Met Ala Thr Lys Met Ala Ala Leu His
785                 790                 795                 800

Tyr Pro Ser Thr Thr Ala Leu Gln Glu Met Val His Gln Val Thr Asp
```

-continued

```
                805                 810                 815
Leu Ser Arg Asn Ala Gln Leu Phe Lys Arg Ser Leu Leu Glu Met Ala
            820                 825                 830
Thr Phe (2) INFORMATION FOR SEQ ID NO:3:

(i) SEQUENCE CHARACTERISTICS:
        (A) LENGTH: 872 amino acids
        (B) TYPE: amino acid
        (C) STRANDEDNESS: Not Relevant
        (D) TOPOLOGY: Not Relevant (ii) MOLECULE TYPE: protein (iii) HYPOTHETICAL: NO (iv) ANTI-SENSE: NO (xi) SEQUENCE DESCRIPTION: SEQ ID NO:3:

Met Lys Tyr Leu Asn Val Leu Ala Lys Ala Leu Tyr Asp Asn Val Ala
1               5                   10                  15

Glu Ser Pro Asp Glu Leu Ser Phe Arg Lys Gly Asp Ile Met Thr Val
            20                  25                  30

Glu Arg Asp Thr Gln Gly Leu Asp Gly Trp Trp Leu Cys Ser Leu His
        35                  40                  45

Gly Arg Gln Gly Ile Val Pro Gly Asn Arg Leu Lys Ile Leu Val Gly
    50                  55                  60

Met Tyr Asp Lys Lys Pro Ala Ala Pro Gly Pro Gly Pro Pro Ala Thr
65                  70                  75                  80

Pro Pro Gln Pro Gln Pro Ser Leu Pro Gln Gly Val His Thr Pro Val
                85                  90                  95

Pro Pro Ala Ser Gln Tyr Ser Pro Met Leu Pro Thr Ala Tyr Gln Pro
            100                 105                 110

Gln Pro Asp Asn Val Tyr Leu Val Pro Thr Pro Ser Lys Thr Gln Gln
        115                 120                 125

Gly Leu Tyr Gln Ala Pro Gly Asn Pro Gln Phe Gln Ser Pro Pro Ala
    130                 135                 140

Lys Gln Thr Ser Thr Phe Ser Lys Gln Thr Pro His His Ser Phe Pro
145                 150                 155                 160

Ser Pro Ala Thr Asp Leu Tyr Gln Val Pro Pro Gly Pro Gly Ser Pro
                165                 170                 175

Ala Gln Asp Ile Tyr Gln Val Pro Pro Ser Ala Gly Thr Gly His Asp
            180                 185                 190

Ile Tyr Gln Val Pro Pro Ser Leu Asp Thr Arg Ser Trp Glu Gly Thr
        195                 200                 205

Lys Pro Pro Ala Lys Val Val Val Pro Thr Arg Val Gly Gln Gly Tyr
    210                 215                 220

Val Tyr Glu Ala Ser Gln Ala Glu Gln Asp Glu Tyr Asp Thr Pro Arg
225                 230                 235                 240

His Leu Leu Ala Pro Gly Ser Gln Asp Ile Tyr Asp Val Pro Pro Val
                245                 250                 255

Arg Gly Leu Leu Pro Asn Gln Tyr Gly Gln Glu Val Tyr Asp Thr Pro
            260                 265                 270

Pro Met Ala Val Lys Gly Pro Asn Gly Arg Asp Pro Leu Leu Asp Val
        275                 280                 285

Tyr Asp Val Pro Pro Ser Val Glu Lys Gly Leu Pro Pro Ser Asn His
```

-continued

```
            290                 295                 300
His Ser Val Tyr Asp Val Pro Pro Ser Val Ser Lys Asp Val Pro Asp
305                 310                 315                 320

Gly Pro Leu Leu Arg Glu Glu Thr Tyr Asp Val Pro Pro Ala Phe Ala
                325                 330                 335

Lys Pro Lys Pro Phe Asp Pro Thr Arg His Pro Leu Ile Leu Ala Ala
                340                 345                 350

Pro Pro Pro Asp Ser Pro Pro Ala Glu Asp Val Tyr Asp Val Pro Pro
                355                 360                 365

Pro Ala Pro Asp Leu Tyr Asp Val Pro Pro Gly Leu Arg Arg Pro Gly
            370                 375                 380

Pro Gly Thr Leu Tyr Asp Val Pro Arg Glu Arg Val Leu Pro Pro Glu
385                 390                 395                 400

Val Ala Asp Gly Ser Val Ile Asp Asp Gly Val Tyr Ala Val Pro Pro
                405                 410                 415

Pro Ala Glu Arg Glu Ala Pro Thr Asp Gly Lys Arg Leu Ser Ala Ser
                420                 425                 430

Ser Thr Gly Ser Thr Arg Ser Ser Gln Ser Ala Ser Ser Leu Glu Val
            435                 440                 445

Val Val Pro Gly Arg Glu Pro Leu Glu Leu Glu Val Ala Val Glu Thr
450                 455                 460

Leu Ala Arg Leu Gln Gln Gly Val Ser Thr Thr Val Ala His Leu Leu
465                 470                 475                 480

Asp Leu Val Gly Ser Ala Ser Gly Pro Gly Gly Trp Arg Ser Thr Ser
                485                 490                 495

Glu Pro Gln Glu Pro Pro Val Gln Asp Leu Lys Ala Ala Val Ala Ala
                500                 505                 510

Val His Gly Ala Val His Glu Leu Leu Glu Phe Ala Arg Ser Ala Val
            515                 520                 525

Ser Ser Ala Thr His Thr Ser Asp Arg Thr Leu His Ala Lys Leu Ser
530                 535                 540

Arg Gln Leu Gln Lys Met Glu Asp Val Tyr Gln Thr Leu Val Val His
545                 550                 555                 560

Gly Gln Val Leu Asp Ser Gly Arg Gly Gly Pro Gly Phe Thr Leu Asp
                565                 570                 575

Asp Leu Asp Thr Leu Val Ala Cys Ser Arg Ala Val Pro Glu Asp Ala
                580                 585                 590

Lys Gln Leu Ala Ser Phe Leu His Gly Asn Ala Ser Leu Leu Phe Arg
            595                 600                 605

Arg Thr Lys Ala Pro Gly Pro Gly Pro Glu Gly Ser Ser Ser Leu His
610                 615                 620

Leu Asn Pro Thr Asp Lys Ala Ser Ser Ile Gln Ser Arg Pro Leu Pro
625                 630                 635                 640

Ser Pro Pro Lys Phe Thr Ser Gln Asp Ser Pro Asp Gly Gln Tyr Glu
                645                 650                 655

Asn Ser Glu Gly Gly Trp Met Glu Asp Tyr Asp Tyr Val His Leu Gln
                660                 665                 670

Gly Lys Glu Glu Phe Glu Lys Thr Gln Lys Glu Leu Leu Glu Lys Gly
            675                 680                 685

Asn Ile Val Arg Gln Gly Lys Gly Gln Leu Glu Leu Gln Gln Leu Lys
            690                 695                 700

Gln Phe Glu Arg Leu Glu Gln Glu Val Ser Arg Pro Ile Asp His Asp
705                 710                 715                 720
```

```
Leu Ala Asn Trp Thr Pro Ala Gln Pro Leu Val Pro Gly Arg Thr Gly
                725                 730                 735

Gly Leu Gly Pro Ser Asp Arg Gln Leu Leu Leu Phe Tyr Leu Glu Gln
            740                 745                 750

Cys Glu Ala Asn Leu Thr Thr Leu Thr Asp Ala Val Asp Ala Phe Phe
            755                 760                 765

Thr Ala Val Ala Thr Asn Gln Pro Pro Lys Ile Phe Val Ala His Ser
    770                 775                 780

Lys Phe Val Ile Leu Ser Ala His Lys Leu Val Phe Ile Gly Asp Thr
785                 790                 795                 800

Leu Ser Arg Gln Ala Lys Ala Ala Asp Val Arg Ser Lys Val Thr His
                805                 810                 815

Tyr Ser Asn Leu Leu Cys Asp Leu Leu Arg Gly Ile Val Ala Thr Thr
                820                 825                 830

Lys Ala Ala Leu Gln Tyr Pro Ser Pro Ser Ala Ala Gln Asp Met
            835                 840                 845

Val Asp Arg Val Lys Glu Leu Gly His Ser Thr Gln Gln Phe Arg Arg
    850                 855                 860

Val Leu Gly Gln Leu Ala Ala Ala
865                 870
```

(2) INFORMATION FOR SEQ ID NO:4:

(i) SEQUENCE CHARACTERISTICS:
        (A) LENGTH: 78 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO:4:

```
Leu Ser Gln Phe Gln Leu Leu Glu Gln Glu Ile Thr Lys Pro Val Glu
1               5                   10                  15

Asn Asp Ile Ser Lys Trp Lys Pro Ser Gln Ser Leu Pro Thr Thr Asn
            20                  25                  30

Asn Ser Val Gly Ala Gln Asp Arg Gln Leu Leu Cys Phe Tyr Tyr Asp
            35                  40                  45

Gln Cys Glu Thr His Phe Ile Ser Leu Leu Asn Ala Ile Asp Ala Leu
    50                  55                  60

Phe Ser Cys Val Ser Ser Ala Gln Pro Pro Arg Ile Phe Val
65                  70                  75
```

SIGNAL MEDIATOR PROTEIN THAT INDUCES CELLULAR MORPHOLOGICAL ALTERATIONS

This application is a continuation of U.S. Ser. No. 08/968,633, filed Nov. 12, 1997, which in turn is a divisional application of U.S. application Ser. No. 08/491,357 filed on Jun. 30, 1995, now issued U.S. Pat. No. 5,716,782, the entirety of each being incorporated by reference herein.

Pursuant to 35 U.S.C. §202(c), it is hereby acknowledged that the U.S. Government has certain rights in the invention described herein, which was made in part with funds from the National Institutes of Health.

FIELD OF THE INVENTION

This invention relates to diagnosis and treatment of neoplastic diseases. More specifically, this invention provides novel nucleic acid molecules, proteins and antibodies useful for detection and/or regulation of complex signalling events leading to morphological and potentially neoplastic cellular changes.

BACKGROUND OF THE INVENTION

Cellular transformation during the development of cancer involves multiple alterations in the normal pattern of cell growth regulation. Primary events in the process of carcinogenesis involve the activation of oncogene function by some means (e.g., amplification, mutation, chromosomal rearrangement), and in many cases the removal of anti-oncogene function. In the most malignant and untreatable tumors, normal restraints on cell growth are completely lost as transformed cells escape from their primary sites and metastasize to other locations in the body. One reason for the enhanced growth and invasive properties of some tumors may be the acquisition of increasing numbers of mutations in oncogenes, with cumulative effect (Bear et al., Proc. Natl. Acad. Sci. USA 86:7495–7499, 1989). Alternatively, insofar as oncogenes function through the normal cellular signalling pathways required for organismal growth and oncogenes function through the normal cellular signalling pathways required for organismal growth and cellular function (reviewed in McCormick, Nature 363:15–16, 1993), additional events corresponding to mutations or deregulation in the oncogenic signalling pathways may also contribute to tumor malignancy (Gilks et al., Mol. Cell Biol. 13:1759–1768, 1993), even though mutations in the signalling pathways alone may not cause cancer.

Several discrete classes of proteins are known to be involved in conferring the different types of changes in cell division properties and morphology associated with transformation. These changes can be summarized as, first, the promotion of continuous cell cycling (immortalization); second, the loss of responsiveness to growth inhibitory signals and cell apoptotic signals; and third, the morphological restructuring of cells to enhance invasive properties.

Of these varied mechanisms of oncogene action, the role of control of cell morphology is one of the least understood. Work using non-transformed mammalian cells in culture has demonstrated that simply altering the shape of a cell can profoundly alter its pattern of response to growth signals (DiPersio et al., Mol. Cell Biol. 11:4405–4414, 1991), implying that control of cell shape may actually be causative of, rather than correlative to, cell transformation. For example, mutation of the antioncogene NF2 leads to development of nervous system tumors. Higher eucaryotic proteins involved in promoting aberrant morphological changes related to cancer may mediate additional functions in normal cells that are not obviously related to the role they play in cancer progression, complicating their identification and characterization. Identification and characterization of such genes and their encoded proteins would be beneficial for the development of therapeutic strategies in the treatment of malignancies.

Recent evidence suggests that certain key proteins involved in control of cellular morphology contain conserved domains referred to as SH2 and SH3 domains. These domains consist of non-catalytic stretches of approximately 50 amino acids (SH3) and 100 amino acids (SH2, also referred to as the "Src homology domain"). SH2/SH3 domains are found in cytoskeletal components, such as actin, and are also found in signalling proteins such as Abl. The interaction of these proteins may play a critical role in organizing cytoskeleton-membrane attachments.

Besides the numerous SH2/SH3 containing molecules with known catalytic or functional domains, there are several signalling molecules, called "adapter proteins," which are so small that no conserved domains seem to exist except SH2 and SH3 domains. Oncoproteins such as Nck, Grb2/Ash/SEM5 and Crk are representatives of this family. The SH2 regions of these oncoproteins bind specific phosphotyrosine-containing proteins by recognizing a phosphotyrosine in the context of several adjacent amino acids. Following recognition and binding, specific signals are transduced in a phosphorylation dependent manner.

As another example, P47v-Crk (CrK) is a transforming gene from avian sarcoma virus isolate CT10. This protein contains one SH2 and one SH3 domain, and induces an elevation of tyrosine phosphorylation on a variety of downstream targets. One of these targets, p130cas, is tightly associated with v-Crk. The SH2 domain of v-Crk is required for this association and subsequent cellular transformation. P130cas is also a substrate for Src mediated phosphorylation. Judging from its structure, p130cas may function as a "signal assembler" of Src family kinases and several cellular SH2-containing proteins. These proteins bind to the SH2 binding domain of p130cas, which is believed to induce a conformational change leading to the activation in inactivation of downstream signals, modulated by multiple domains of the protein.

Another oncogene, Ras, is a member of a large evolutionarily conserved superfamily of small GTP-binding proteins responsible for coordinating specific growth factor signals with specific changes in cell shape, including the development of stress fibers and membrane ruffles (Ridley and Hall, Cell 70:389–399, 1992; Ridley et al., Cell 70:401–410,1992). A rapidly growing family of oncoproteins, including Vav, Bcr, Ect-2, and Dbl, has been found to be involved in a variety of different tumors (Eva and Aaronson, Nature 316:273–275, 1985; Ron et al., EMBO J. 7:2465–2473, 1988; Adams et al., Oncogene 7:611–618, 1992; Miki et al., Nature 362:462–465, 1993). Proteins of this family have been shown to interact with Ras/Rac/Rho family members, and possess sequence characteristics that suggest they too directly associate with and modulate organization of the cytoskeleton.

In view of the significant relationship between signalling or "adapter" proteins, altered cellular morphology and the development of cancer, it would be of clear benefit to identify and isolate such proteins (or genes encoding them) for the purpose of developing diagnostic/therapeutic agents for the treatment of cancer. It is an object of the present invention to provide a purified nucleic acid molecule of mammalian origin that encodes a signal mediator protein (SMP) involved in the signalling cascade related to morphological cellular changes, and therefrom provide isolated and purified protein. Such a gene, when expressed in model systems, such as yeast, will provide utility as a research tool for identifying genes encoding interacting proteins in the signalling cascade thereby facilitating the elucidation of the gene may also be used diagnostically to identify related genes, and therapeutically in gene augmentation or replacement treatments. It is a further object of the present invention to provide derivatives of the SMP-encoding nucleic acid, such as various oligonucleotides and nucleic acid fragments for use as probes or reagents to analyze the expression of genes encoding the proteins. It is a further object of the invention to provide the signal mediator protein in purified form, and to provide antibodies immunologically specific for the signal mediator protein for the purpose of identifying and quantitating this mediator in selected cells and tissues.

SUMMARY OF THE INVENTION

This invention provides novel biological molecules useful for identification, detection and/or regulation of complex signalling events that regulate cellular morphological changes. According to one aspect of the present invention, an isolated nucleic acid molecule is provided that includes an open reading frame encoding a mammalian signal mediator protein of a size between about 795 and about 875 amino acids in length (preferably about 834 amino acids). The protein comprises an amino-terminal SH3 domain, an internal domain that includes a multiplicity of SH2 binding motifs, and a carboxy-terminal effector domain. When produced in Saccharomyces cerevisiae, the carboxy-terminal effector domain is capable of inducing pseudohyphal budding in the organism under predetermined culture conditions. In a preferred embodiment, an isolated nucleic acid molecule is provided that includes an open reading frame encoding a human mammalian signal mediator protein. In a particularly preferred embodiment, the human signal mediator protein has an amino acid sequence substantially the same as Sequence I.D. No. 2. A mediator protein has an amino acid sequence substantially the same as Sequence I.D. No. 2. An exemplary nucleic acid molecule of the invention comprises Sequence I.D. No. 1.

According to another aspect of the present invention, an isolated nucleic acid molecule is provided, which has a sequence selected from the group consisting of: (1) Sequence I.D. No. 1; (2) a sequence hybridizing with part or all of the complementary strand of Sequence I.D. No. 1 and encoding a polypeptide substantially the same as part or all of a polypeptide encoded by Sequence I.D. No. 1; and (3) a sequence encoding part or all of a polypeptide having amino acid Sequence I.D. No. 2.

According to another aspect of the present invention, an isolated nucleic acid molecule is provided which has a sequence that encodes a carboxy-terminal effector domain of a mammalian signal mediator protein. This domain has an amino acid sequence of greater than 74% similarity to the portion of Sequence I.D. No. 2 comprising amino acids 626–834.

According to another aspect of the present invention, an isolated mammalian signal mediator protein is provided which has a deduced molecular weight of between about 100 kDa and 115 kDa (preferably about 108 kDa). The protein comprises an amino-terminal SH3 domain, an internal domain that includes a multiplicity of SH2 binding motifs, and a carboxy-terminal effector domain, which is capable of inducing pseudohyphal budding in Saccharomyces cerevisiae under pre-determined culture conditions, as described in greater detail hereinbelow. In a preferred embodiment of the invention, the protein is of human origin, and has an amino acid sequence substantially the same as Sequence I.D. No. 2.

According to another aspect of the present invention, an isolated mammalian signal mediator protein is provided, which comprises a carboxy-terminal effector domain having an amino acid sequence of greater than 74% similarity to the portion of Sequence I.D. No. 2 comprising amino acids 626–834. In a preferred embodiment, the amino acid sequence of the carboxy-terminal effector domain is greater than about 50% identical to that portion of Sequence I.D. No. 2.

According to another aspect of the present invention, antibodies immunologically specific for the proteins described hereinabove are provided.

Various terms relating to the biological molecules of the present invention are used hereinabove and also throughout the specifications and claims. The terms "substantially the same," "percent similarity" and "percent identity (identical)" are defined in detail in the description set forth below.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a procaryote or eucaryote.

With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "substantially pure" refers to a preparation comprising at least 50–60% by weight the compound of interest (e.g., nucleic acid, oligonucleotide, protein, etc.). More preferably, the preparation comprises at least 75% by weight, and most preferably 90–99% by weight, the compound of interest. Purity is measured by methods appropriate for the compound of interest (e.g. chromatographic methods, agarose or polyacrylamide gel electrophoresis, HPLC analysis, and the like).

With respect to antibodies of the invention, the term "immunologically specific" refers to antibodies that bind to one or more epitopes of a protein of interest (e.g., SMP), but which do not substantially recognize and bind other molecules in a sample containing a mixed population of antigenic biological molecules.

With respect to oligonucleotides, the term "specifically hybridizing" refers to the association between two single-stranded nucleotide molecules of sufficiently complementary sequence to permit such hybridization under predetermined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The nucleic acids, proteins and antibodies of the present invention are useful as research tools and will facilitate the elucidation of the mechanistic action of the novel genetic and protein interactions involved in the control of cellular morphology. They should also find broad utility as diagnostic and therapeutic agents for the detection and treatment of cancer and other proliferative diseases.

BRIEF DESCRIPTION OF THE DRAWINGS

FIGS. 1A–1D. Nucleotide sequence (Sequence I.D. No. 1) and deduced amino acid sequence (Sequence I.D. No. 2) of HEF1, a cDNA of human origin encoding an exemplary signal mediator protein of the invention.

FIG. 2. Amino acid sequence alignment of the deduced amino acid sequence of HEF1 (Sequence I.D. No. 2) with homologous sequences of p130cas from rat (Sequence I.D. No 3). Boxes represent regions of sequence identity between the two proteins. The closed circle marks the site of the initial methionine in the truncated clone of HEF1. The thick underline denotes the conserved SH3 domain. Tyrosines are marked with asterisks.

FIG. 3. Amino acid sequence alignment of the carboxy-terminal regions of HEF1-encoded hSMP with p130cas and the mouse homolog of hSMP, mSMP encoded by MEF1 (Sequence I.D. No. 4).

DETAILED DESCRIPTION OF THE INVENTION

In accordance with the present invention, a novel gene has been isolated that encodes a protein involved in the signal transduction pathway that coordinates changes in cellular growth regulation. This protein is sometimes referred to herein as "signal mediator protein or "SMP."

Using a screen to identify human genes that promote psuedohyphal conversion in the yeast *Saccharomyces cerevisiae*, a 900 bp partial CDNA clone was obtained that causes strong pseudohyphal growth of *S. cerevisiae* on low nitrogen medium. This dimorphic shift from normal to "pseudohyphal" budding in yeast has been shown to involve the action of growth regulatory kinase cascades and cell cycle-related transcription factors (Gimeno & Fink, Mol. Cell Biol. 14: 2100–2112, 1994; Gimeno et al., Cell 68: 1077–1090, 1992; Blacketer et al., Mol. Cell Biol. 13: 5567–5581, 1993; Liu et al. Science 262: 1741–1744, 1993).

Using the 900 bp partial CDNA clone as a probe in a combination of screening approaches, a full-length clone of approximately 3.7 kb was isolated. This clone encodes a single continuous open reading frame of about 834 amino acids, which constitutes the signal mediator protein of the invention. SMP is characterized by an amino-terminal SH3 domain and an adjacent domain containing multiple SH2 binding motifs. The protein also contains a carboxy terminal "effector" domain that is capable of inducing the shift to pseudohyphal budding in yeast. A cDNA encoding a mouse homolog of the carboxy-terminal "effector" region has also been identified (FIG. 3). Homology searches of the Genbank data base revealed an approximately 64% similarity on the amino acid level between SMP from human and the adapter protein, p130cas, recently cloned from rat (as disclosed by Sakai et al., EMBO J. 13: 3748–3756, 1994). However, p130cas is significantly larger than SMP (968 amino acids for rat p130cas versus 834 amino acids for human SMP), and differs with respect to amino acid composition. A comparison of SMP with p130cas is set forth in greater detail in Example 1.

The aforementioned human partial cDNA clone that enhanced pseudohyphal formation in yeast encodes only the carboxy-terminal portion of SMP, comprising about 182 amino acids. The enhancement of pseudohyphal formation by the carboxy-terminal fragment of SMP, in addition to the relatively high degree of homology with p130cas over this region, indicates that it is this domain that acts as an effector in regulating cellular morphology. Thus, this domain is sometimes referred to herein as a "C-terminal effector domain." It should be noted that, although the carboxy-terminal fragment of p130cas was also found capable of enhancing pseudohyphal formation, it did not do so to the same extent as the C-terminal domain of SMP (on a scale of 1 to 10, the SMP C-terminal domain is a "10," while the p130cas C-terminal domain is a "6"). The SMP C-terminal domain was also found to be involved in homodimerization and in heterodimerization with p130cas and, like p130cas, associates with Abl and appears to be phosphorylated by Abl.

Thus, SMP can be classified within a family of docking adapters, which includes p130cas, capable of multiple associations with signalling molecules and transduction of such signals to coordinate changes in cellular growth regulation. The SMP protein comprises, from amino- to carboxy-terminus, an SH3 domain, a polyproline domain several SH2 binding motifs, a serine rich region, and the carboxy-terminal effector domain.

A human clone that encodes an exemplary signal mediator protein of the invention is sometimes referred to herein as "HEF1" (human enhancer of filamentation) to reflect the screening method by which it was in part identified. The nucleotide sequence of HEF1 is set forth herein as Sequence I.D. No. 1. The signal mediator protein encoded by HEF1 is sometimes referred to herein as hSMP. The amino acid sequence deduced from Sequence I.D. No. 1 is set forth herein as Sequence I.D. No. 2. The characteristics of human SMP are described in greater detail in Example 1.

It is believed that Sequence I.D. No. 1 constitutes a full-length SMP-encoding clone as it contains a suitable methionine for initiation of translation. This CDNA is approximately 3.7 kb in length. Northern analysis of a human multi-tissue RNA blot (Clontech MTNI) suggests a full-length transcript of approximately 3.4 kb. A second transcript of approximately 5.4 kb was also observed, which may represent an alternative splice or initiation site.

Although the human SMP-encoding gene, HEF1, is described and exemplified herein, this invention is intended to encompass nucleic-acid sequences and proteins from other species that are sufficiently similar to be used interchangeably with SMP-encoding nucleic acids and proteins for the research, diagnostic and therapeutic purposes described below. Because of the high degree of conservation of genes encoding specific signal transducers and related oncogenes, it will be appreciated by those skilled in the art that, even if the interspecies SMP homology is low, SMP-encoding nucleic acids and SMP proteins from a variety of mammalian species should possess a sufficient degree of homology with SMP so as to be interchangeably useful with SMP in such diagnostic and therapeutic applications. Accordingly, the present invention is drawn to mammalian SMP-encoding nucleic acids and SMP proteins, preferably to SMP of primate origin, and most preferably to SMP of human origin. Accordingly, when the terms "signal mediator protein" or "SMP" or "SMP-encoding nucleic acid" are used herein, they are intended to encompass mammalian SMP-encoding nucleic acids and SMPs falling within the confines of homology set forth below, of which hSMP, preferably encoded by HEF1, is an exemplary member.

Allelic variants and natural mutants of Sequence I.D. No. 1 are likely to exist within the human genome and within the genomes of other mammalian species. Because such variants are expected to possess certain differences in nucleotide and amino acid sequence, this invention provides an isolated nucleic acid molecule and an isolated SMP protein having at least about 50–60% (preferably 60–80%, most preferably over 80%) sequence homology in the coding region with the nucleotide sequence set forth as Sequence I.D. No. 1 (and, preferably, specifically comprising the coding region of sequence I.D. No. 1), and the amino acid sequence of Sequence I.D. No. 2. Because of the natural sequence variation likely to exist among signal mediator proteins and nucleic acids encoding them, one skilled in the art would expect to find up to about 40–50% sequence variation, while still maintaining the unique properties of the SMP of the present invention. Such an expectation is due in part to the degeneracy of the genetic code, as well as to the known evolutionary success of conservative amino acid sequence variations, which do not appreciably alter the nature of the protein. Accordingly, such variants are considered substantially the same as one another and are included within the scope of the present invention.

For purposes of this invention, the term "substantially the same" refers to nucleic acid or amino acid sequences having sequence variation that do not materially affect the nature of the protein (i.e. the structure and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function. The terms "percent identity" and "percent similarity" are also used herein in comparisons among amino acid sequences. These terms are intended to be defined as they are in the UWGCG sequence analysis program (Devereaux et al., Nucl. Acids Res. 12: 387–397, 1984), available from the Unversity of Wisconsin.

The following description sets forth the general procedures involved in practicing the present invention. To the extent that specific materials are mentioned, it is merely for purposes of illustration and is not intended to limit the invention. Unless otherwise specified, general cloning procedures, such as those set forth in Sambrook et al., *Molecular Cloning*, Cold Spring Harbor Laboratory (1989) (hereinafter "Sambrook et al.") are used.

I. Preparation of SMP-Encoding Nucleic Acid Molecules, Signal Mediator Proteins and Antibodies Thereto A. Nucleic Acid Molecules Nucleic acid molecules encoding the SMPs of the invention may be prepared by two general methods: (1) They may be synthesized from appropriate nucleotide triphosphates, or (2) they may be isolated from biological sources. Both methods utilize protocols well known in the art.

The availability of nucleotide sequence information such as the full length cDNA having Sequence I.D. No. 1, enables preparation of an isolated nucleic acid molecule of the invention by oligonucleotide synthesis. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a 3.7 kb double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire-3.7 kb double-stranded molecule. A synthetic DNA molecule so constructed may then be cloned and amplified in an appropriate vector.

Nucleic acid sequences encoding SMP may be isolated from appropriate biological sources using methods known in the art. In a preferred embodiment, a cDNA clone is isolated from an expression library of human origin. In an alternative embodiment, human genomic clones encoding SMP may be isolated. Alternatively, cDNA or genomic clones encoding from other mammalian species may be obtained.

In accordance with the present invention, nucleic acids having the appropriate level sequence homology with the protein coding region of Sequence I.D. No. 1 may be identified by using hybridization and washing conditions of appropriate stringency. For example, hybridizations may be performed, according to the method of Sambrook et al., using a hybridization solution comprising: 5X SSC, 5X Denhardt's reagent, 1.0% SDS, 100 $\mu$g/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2X SSC and 1% SDS; (2) 15 minutes at room temperature in 2X SSC and 0.1% SDS; (3) 30 minutes–1 hour at 37° C. in 1X SSC and 1% SDS; (4) 2 hours at 42–65° in 1X SSC and 1% SDS, changing the solution every 30 minutes.

Nucleic acids of the present invention may be maintained as DNA in any convenient cloning vector. In a preferred embodiment, clones are maintained in plasmid cloning/expression vector, such as pBluescript (Stratagene, La Jolla, Calif.), which is propagated in a suitable *E. coli* host cell.

SMP-encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments of the CDNA having Sequence I.D. No. 1. Such oligonucleotides are useful as probes for detecting SMP genes in test samples of potentially malignant cells or tissues, e.g. by PCR amplification, or for the isolation of homologous regulators of morphological control.

B. Proteins

A full-length SMP of the present invention may be prepared in a variety of ways, according to known methods. The protein may be purified from appropriate sources, e.g., human or animal cultured cells or tissues, by immunoaffinity purification. However, this is not a preferred method due to the low amount of protein likely to be present in a given cell type at any time.

The availability of nucleic acids molecules encoding SMP enables production of the protein using in vitro expression methods known in the art. For example, a CDNA or gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or BRL, Rockville, Md.

Alternatively, according to a preferred embodiment, larger quantities of SMP may be produced by expression in a suitable procaryotic or eucaryotic system. For example, part or all of a DNA molecule, such as the cDNA having Sequence I.D. No. 1, may be inserted into a plasmid vector adapted for expression in a bacterial cell, such as *E. coli*, or into a baculovirus vector for expression in an insect cell. Such vectors comprise the regulatory elements necessary for expression of the DNA in the bacterial host cell, positioned in such a manner as to permit expression of the DNA in the host cell. Such regulatory elements required for expression include promoter sequences, transcription initiation sequences and, optionally, enhancer sequences.

The SMP produced by gene expression in a recombinant procaryotic or eucaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein. Such methods are commonly used by skilled practitioners.

The signal mediator proteins of the invention, prepared by the aforementioned methods, may be analyzed according to standard procedures. For example, such proteins may be subjected to amino acid sequence analysis, according to known methods.

The present invention also provides antibodies capable of immunospecifically binding to proteins of the invention. Polyclonal antibodies directed toward SMP may be prepared according to standard methods. In a preferred embodiment, monoclonal antibodies are prepared, which react immunospecifically with various epitopes of SMP. Monoclonal antibodies may be prepared according to general methods of Köhler and Milstein, following standard protocols. Polyclonal or monoclonal antibodies that immunospecifically interact with SMP can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules. Other uses of anti-SMP antibodies are described below.

II. Uses of SMP-Encoding Nucleic Acids, Signal Mediator Proteins and Antibodies Thereto Cellular signalling molecules have received a great deal of attention as potential prognostic indicators of neoplastic disease and as therapeutic agents to be used for a variety of purposes in cancer chemotherapy. As a signalling molecule that induces profound morphological changes, SMP and related proteins from other mammalian species promise to be particularly useful research tools, as well as diagnostic and therapeutic agents.

A. SMP-Encoding Nucleic Acids

SMP-encoding nucleic acids may be used for a variety of purposes in accordance with the present invention. SMP-encoding DNA, RNA, or fragments thereof may be used as probes to detect the presence of and/or expression of genes encoding SMP. Methods in which SMP-encoding nucleic acids may be utilized as probes for such assays include, but are not limited to: (1) in situ hybridization; (2) Southern hybridization (3) northern hybridization; and (4) assorted amplification reactions such as polymerase chain reactions (PCR).

The SMP-encoding nucleic acids of the invention may also be utilized as probes to identify related genes either from humans or from other species. As is well known in the art, hybridization stringencies may be adjusted to allow hybridization of nucleic acid probes with complementary sequences of varying degrees of homology. Thus, SMP-encoding nucleic acids may be used to advantage to identify and characterize other genes of varying degrees of relation to SMP, thereby enabling further characterization the signalling cascade involved in the morphological control of different cell types. Additionally, they may be used to identify genes encoding proteins that interact with SMP (e.g., by the "interaction trap" technique), which should further accelerate elucidation of these cellular signalling mechanisms.

Nucleic acid molecules, or fragments thereof, encoding SMP may also be utilized to control the expression of SMP, thereby regulating the amount of protein available to participate in oncogenic signalling pathways. Alterations in the physiological amount of "adapter protein" may act synergistically with chemotherapeutic agents used to treat cancer. In one embodiment, the nucleic acid molecules of the invention may be used to decrease expression of SMP in a population of malignant cells, In this embodiment, SMP proteins would be unable to serve as substrate acceptors for phosphorylation events mediated by oncogenes thereby effectively abrogating the activation signal. In this embodiment, antisense oligonucleotides expression. The use of antisense oligonucleotides to decrease expression levels of a pre-determined gene is known in the art. In a preferred embodiment, such antisense oligonucleotides are modified in various ways to increase their stability and membrane permeability, so as to maximize their effective delivery to target cells in vitro and in vivo. Such modifications include the preparation of phosphorothioate or methylphosphonate derivatives, among many others, according to procedures known in the art.

In another embodiment, overexpression of SMP is induced in a target population of cells to generate an excess of signal adapter molecules. This excess allows SMP to serve as a phosphorylation "sink" for the kinase activity of transforming oncogenes. overexpression of SMP could lead to alterations in the cytoskeleton which could then be monitored with immunofluorescence or any other standard technique known in the art. Alternatively, overexpression of SMP by this method may facilitate the isolation and characterization of other components involved in the protein—protein complex formation that occurs via the SH2 homology domains during signal transduction.

As described above, SMP-encoding nucleic acids are also used to advantage to produce large quantities of substantially pure SMP protein, or selected portions thereof. In a preferred embodiment, the C-terminal "effector domain" of SMP is produced by expression of a nucleic acid encoding the domain. The full-length protein or selected domain is thereafter used for various research, diagnostic and therapeutic purposes, as described below.

B. Signal Mediator Protein and Antibodies

Purified SMP, or fragments thereof, may be used to produce polyclonal or monoclonal antibodies which also may serve as sensitive detection reagents for the presence and accumulation of SMP (or complexes containing SMP) in cultured cells or tissues from living patients (the term "patients" refers to both humans and animals). Recombinant techniques enable expression of fusion proteins containing part or all of the SMP protein. The full length protein or fragments of the protein may be used to advantage to generate an array of monoclonal antibodies specific for various epitopes of the protein, thereby providing even greater sensitivity for detection of the protein in cells or tissue.

Polyclonal or monoclonal antibodies immunologically specific for SMP may be used in a variety of assays designed to detect and quantitate the protein, which may be useful for rendering a prognosis as to a malignant disease. Such assays include, but are not limited to: (1) flow cytometric analysis; (2) immunochemical localization in SMP in cultured cells or tissues; and (3) immunoblot analysis (e.g., dot blot, Western blot) of extracts from various cells and tissues. Additionally, as described above, anti-SMP can be used for purification of SMP (e.g., affinity column purification, immunoprecipitation).

Anti-SMP antibodies may also be utilized as therapeutic agents to block the normal functionality of SMP in a target cell population, such as a tumor. Thus, similar to the antisense oligonucleotides described above, anti-SMP antibodies may be delivered to a target cell population by methods known in the art (i.e. through various lipophilic carriers that enable delivery of the compound of interest to the target cell cytoplasm) where the antibodies may interact with intrinsic SMP to render it nonfunctional.

From the foregoing discussion, it can be seen that SMP-encoding nucleic acids and SMP proteins of the invention can be used to detect SMP gene expression and protein accumulation for purposes of assessing the genetic and protein interactions involved in the regulation of morphological control pathways of a cell or tissue sample. Aberrant morphological changes are often correlatable with metastatic cellular proliferation in various cancers, such as breast cancer. It is expected that these tools will be particularly useful for diagnosis and prognosis of human neoplastic disease. Potentially of greater significance, however, is the utility of SMP-encoding nucleic acids, proteins and antibodies as therapeutic agents to disrupt the signal transduction pathways mediated by activated oncogenes that result in aberrant morphological cellular alterations.

Although the compositions of the invention have been described with respect to human diagnostics and therapeutics, it will be apparent to one skilled in the art that these tools will also be useful in animal and cultured cell experimentation with respect to various malignancies and/or other conditions manifested by alterations in cellular morphology. As diagnostic agents they can be used to monitor the effectiveness of potential anti-cancer agents on signal transduction pathways mediated by oncogenic proteins in vitro, and/or the development of neoplasms or malignant diseases in animal model systems. As therapeutics, they can be used either alone or as adjuncts to other chemotherapeutic drugs in animal models and veterinary applications to improve the effectiveness of such anti-cancer agents.

The following Example is provided to describe the invention in further detail. This Example is intended to illustrate and not to limit the invention.

EXAMPLE 1

Isolation and Characterization of a Nucleic Acid Molecule Encoding Human SMP

In this Example, we describe the cloning of a cDNA molecule encoding human SMP. This cDNA is sometimes referred to herein as HEF1 for human enhancer of filamentation, because of its identification in the pseudohyphal screen. We also provide an analysis of the structure of the human SMP (hSMP) as predicted from the deduced amino acid sequence encoded by the cDNA. Additionally, we describe the antibodies immunospecific for the recombinant hSMP protein, and their use in immunological detection of phosphorylated SMP from normal and Abl transformed NIH3T3 cells.

Isolation of cDNA and cloning

A HeLa cDNA library constructed in the TRP1+vector JG4-4 (Gyuris et al., Cell 75:791–803), was translated with inserts expressed as native proteins under the control of the galactose-inducible GAL1 promoter, into CGx74 yeast (MATa/α trp1/trp1; see Gimeno et al., 1992, supra). TRP+ transformants were plated to the nitrogen-restricted SLAGR medium (like SLAD, but with 2% galactose, 1% raffinose as a carbon source), and 120,000 colonies were visually screened using a Wild dissecting microscope at 50× amplification to identify colonies that produced pseudohyphae more extensively than background cDNAs from these colonies were isolated and retransformed to naive CGx74; those that reproducibly generated enhanced pseudohyphae were sequenced. A 900 bp cDNA encoding a 182 amino acid open reading frame corresponding to the COOH-terminus of hSMP (HEF1-Cterm 182) possessed the most dramatic phenotype of cDNA obtained in this screen. Using the original 900 bp cDNA isolated in the pseudohyphal screen to probe a placental cDNA library cloned in lambda gt11, a larger clone (3.4 kb) was isolated. The longer clone obtained in this screen was used as a basis for 5' RACE using a kit from Clontech containing RACE-ready CDNA prepared from human kidney. Three independent clones from the RACE approach yielded identical 5' end-points located 18 base pairs upstream of the ATG encoding the first methionine in the sequence shown in FIG. 1. Repeated efforts with multiple primer sets showed no-evidence for an N-terminally extended sequence. The full length clone, HEF1, is about 3.7 kb and encodes a protein about 835 amino acids in length.

Sequence Analysis

Both strands of the HEF1 clone were sequenced using oligonucleotide primers to the JG4-4 vector and to internal HEF1 sequences in combination with the Sequenase system (United States Biochemical) Database searching was performed using the BLAST algorithm (Altschul et al., J. Mol. Biol. 215:403–410, 1990) and sequence analysis was carried out using the package of programs from UWGCG (Devereux et al., Nucl. Acids Res. 12:387–397, 1984).

Northern Analysis

HEF1 CDNA was labelled with $^{32}$P-dCTP by random priming, and used to probe a Northern blot containing 2 μg/lane human mRNA from multiple tissues. The blot was stripped and reprobed with a $^{32}$P-labelled oligonucleotide specific for actin as a control for equivalent loading.

Immunoprecipitation and Western Blotting

Immunoprecipitation of hSMP from normal and Abl transformed NIH 3T3 cells was accomplished using polyclonal antiserum raised against a peptide derived from the hSMP C-terminus. Immunoprecipitates were resolved by electrophoresis on a 12% SDS-polyacrylamide gel. Following electrophoresis, immunoprecipitates were transferred to nitrocellulose, and reprobed with anti-phosphotyrosine antibody (4G10).

Growth Profiles

Yeast were transformed with HEF1 or vector alone and grown to saturated overnight cultures in trp⁻ glucose defined minimal medium, and re-diluted to OD600 <0.05 in trp⁻ galactose for growth curves. Growth curves were performed, with readings taken at 90 minute intervals for 12 hours, and at less frequent intervals up to 48 hours or longer.

Interaction Trap or Two Hybrid Analysis

EGY48 yeast (Gyuris et al., 1993, supra) were transformed by standard methods with plasmids expressing LexA-fusions, activation-domain fusions, or both, together with the LexA operator-LacZ reporter SH18-34 (Gyuris et al., 1993, supra). For all fusion proteins, synthesis of a fusion protein of the correct length in yeast was confirmed by Western blot assays of yeast extracts (Samson et al., Cell 57: 1045–1052, 1989) using polyclonal antiserum specific for LexA (Brent and Ptashne, Nature 312: 612–615, 1984) or for hemagglutinin (Babco, Inc), as appropriate. Activation of the LacZ reporter was determined as previously described (Brent and Ptashne, Cell 43: 729–736, 1985). Beta-galactosidase assays were performed on three independent colonies, on three separate occasions, and values for particular plasmid combinations varied less than 25%. Activation of the LEU2 reporter was determined by observing the colony forming ability of yeast plated on complete minimal medium lacking leucine. The LexA-PRD/HD expressing plasmid has been described (Golemis and Brent, Mol. Cell Biol. 12: 3006–3014, 1992).

RESULTS

Overexpression of the C-terminal domain of SMP influences Saccharomyces cerevisiae cell morphology. To identify proteins that regulate the morphology and polarity of human cells, a human CDNA library was screened for genes which enhanced formation of pseudohyphae when expressed in S. cerevisiae. The yeast undergoes a dimorphic shift in response to severe nitrogen limitation that involves changes in budding pattern, cell cycle control, cell elongation, and invasive growth into agar (Gimeno et al., 1992, supra). A galactose-inducible HeLa cell CDNA library was used to transform a yeast strain that can form pseudohyphae on nitrogen-restricted media, and a number of human genes which specifically enhanced pseudohyphal formation were identified. One of the cDNAs derived from this screen was found to cause the constitutive formation of pseudohyphae on rich and nitrogen restricted media. This cDNA is sometimes referred to as "HEF1-Cterm182" (because it encodes 182 amino acids of the C-terminal domain of the human SMP). A full-length clone containing the cDNA sequence was thereafter obtained. Analysis of the sequence of this CDNA (Sequence I.D. No. 1; FIG. 1) revealed that it was a novel human gene with strong sequence similarity to the rat p130cas gene (as disclosed by Sakai et al. EMBO J. 13: 3748–3756, 1994). This gene was designated HEF1, and its encoded protein was designated hSMP (Sequence I.D. No. 2). A comparison of the amino acid compositions (% by weight) of the HEF1-encoded hSMP and the rat p130cas is shown in Table 1 below.

TABLE 1

| Amino Acid | % Composition | |
|---|---|---|
| | hSMP | p130cas |
| Alanine | 4.3 | 6.2 |
| Arginine | 6.1 | 7.5 |
| Asparagine | 4.1 | 1.8 |
| Aspartic acid | 5.6 | 6.5 |
| Cysteine | 1.5 | 0.6 |
| Glutamine | 8.3 | 8.1 |
| Glutamic acid | 6.6 | 5.8 |
| Glycine | 3.5 | 4.5 |
| Histidine | 4.0 | 3.1 |
| Isoleucine | 4.2 | 1.6 |
| Leucine | 8.7 | 9.6 |
| Lysine | 6.2 | 4.8 |
| Methionine | 2.8 | 1.0 |
| Phenylalanine | 3.2 | 1.6 |
| Proline | 7.0 | 11.1 |
| Serine | 6.6 | 6.7 |
| Threonine | 4.8 | 4.9 |
| Tryptophan | 1.1 | 1.1 |
| Tyrosine | 4.8 | 4.7 |
| Valine | 5.6 | 7.7 |

The deduced length of HEF1-encoded hSMP is 834 amino acids and its deduced molecular weight is about 107,897 Da. The deduced length of the rat p130cas is 968 amino acids and its deduced molecular weight is about 121,421 Da.

Tissue specific expression of HEF1. RNA production was assessed by Northern blot analysis. HEF1 is expressed as two predominant transcripts of approximately 3.4 and 5.4 kb. Although present in all tissues examined (heart, brain, placenta, lung, liver, skeletal muscle, kidney and pancreas), these transcripts are present at significantly higher levels in kidney, lung, and placenta. In contrast, a more uniform distribution throughout the body has been reported for p130cas. Two other cross-hybridizing minor species were detected, migrating at 8.0 kb in lung and 1.2 kb in liver. These may represent alternatively spliced HEF1 transcripts or other HEF1/p130cas related genes. HEF1 represents a distinct gene from p130cas. rather than a human homolog, inasmuch as a screen of a murine genomic library with HEF1 cDNA led to identification of an exon that encoded a mouse C-terminal effector protein having a sequence essentially identical to hSMP-Cterm182 (FIG. 3). Furthermore, probe of a zoo blot at high stringency with a HEF1 CDNA probe indicates this gene is highly conserved from humans to yeast.

hSMP does not induce constitutive pseudohyphal budding by causing severe cell stress. The possibility that the C-terminal domain of hSMP was enhancing pseudohyphae formation by causing severe cell stress was excluded by comparing the growth rates of yeast containing the HEF1-cterm182 cDNA to yeast containing the expression vector control on plates and in liquid culture, with galactose as a sugar source to induce expression of HEF1-cterm182. The growth rate data shows that SMP-encoding genes are not simply toxic to yeast.

Figure 2:
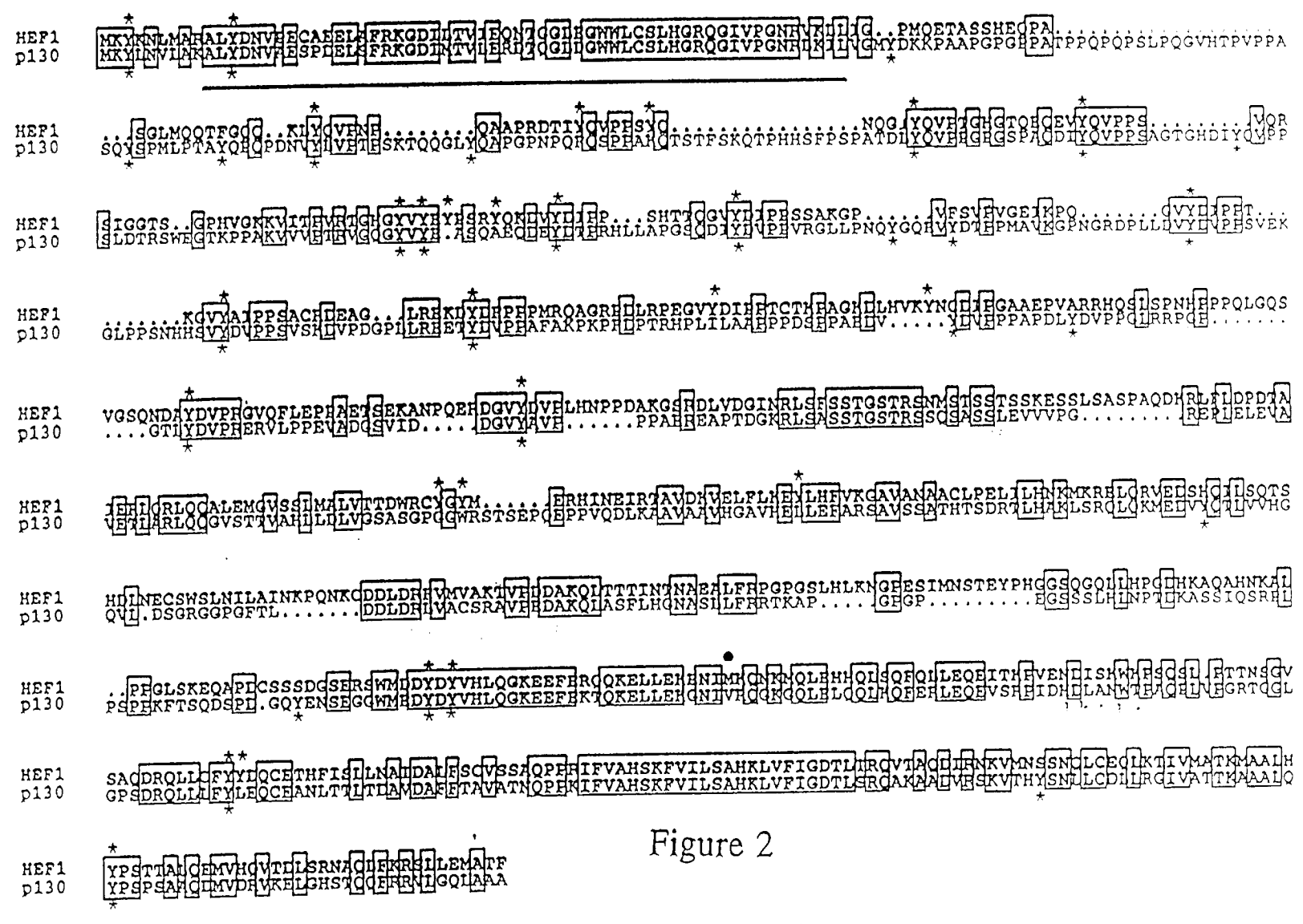

SMP belongs to a class of "adapter proteins" important in signalling cascades influencing morphological control. The HEF1 gene is approximately 3.7 kb and encodes a single continuous open reading frame of about 835 amino acids. The predicted hSMP protein notably contains an amino-terminal SH3 domain and an adjacent domain containing multiple SH2 binding motifs. Homology search of the Genbank database revealed that hSMP is 64% similar at the amino acid level to the adapter protein p130cas, recently cloned from rat (Sakai et al., EMBO J. 13:3748–3756, 1994). The amino acid alignment of hSMP and p130cas is shown in FIG. 2. P130cas was determined to be the predominant phosphorylated species in cells following transformation by the oncoprotein Crk and also complexes with, and is a substrate for Abl and Src. As shown in Table 2 below, the homology between SMP and p130cas is most pronounced over the SH3 domain (92% similarity, 74% identity) and in the region corresponding to the SMP-Cterm182 fragment (74% similarity, 57% identity). Although the domain containing SH2-binding motifs is more divergent from p130cas, SMP similarly possesses a large number of tyrosines in this region. The majority of SH2 binding sites in p130cas match the consensus for the SH2 domain of the oncoprotein Crk, while the amino acids flanking the tyrosine residues in SMP are more diverse, suggesting a broader range of associating proteins. Various SH2 binding motifs conserved between hSMP and p130cas are shown in Table 3.

TABLE 2

Domain Alignment: hSMP and p130cas
(Domains from amino to carboxyl terminus down the Table)

| Domain | Size (a.a.) hSMP | Size (a.a.) p130cas | % Similarity/Identity (hSMP:p130cas) |
|---|---|---|---|
| SH3 | 50 | 50 | 92% similar, 74% identical |
| Polyproline | 10 | 38 | (not compared) |
| SH2 binding motifs | 290 | 410 | 55% similar, 36% identical |
| Serine-rich region | 250 | 260 | 56% similar, 35% identical |
| C-terminal effector domain | 210 | 210 | 74% similar, 57% identical |

TABLE 3

Conserved SH2 Binding Motifs and Associating Proteins

| SH2 Binding Motif | Associating Proteins |
|---|---|
| YDIP, YDVP, YDFP | Crk |
| YEYP, YAIP, YQNQ | Vav or fps/fes, Abl, Grb2 |
| YQVP, YQKD, YVYE, YPSR, YNCD | Novel |

The enhancement of pseudohyphal formation by hSMP-Cterm182 fragment in addition to the relatively high degree of homology to p130cas suggests that this domain acts as an effector in regulating cellular morphology. A test was performed to assay whether the homologous region of p130cas also enhanced pseudohyphal formation. The results show that the C-terminal fragment of p130cas did enhance psuedohyphal formation but not to the same extent as the C-terminal fragment of SMP. SMP was found to induce the strongest pseudohyphal phenotype of only cDNA fragment. By comparison, p130cas and another pseudohyphal inducer, RBP7 (subunit 7 of human RNA polymerase II, Golemis et al., Mol. Biol. of the Cell, 1995, in press) were only about 60% as effective as the hSMP-Cterm182 fragment.

The possible functions for the novel carboxy-terminal domains were investigated further using two-hybrid analysis. These experiments revealed that this domain mediated SMP homodimerization, and SMP/p130cas heterodimerization, yet failed to interact with non-specific control proteins.

SMP is a substrate for oncogene mediated phosphorylation. SMP was immunoprecipitated from normal and v-Abl transformed NIH3T3 cells using polyclonal antisera raised against a MAP peptide derived from the hSMP C-terminal domain. Probe of these immunoprecipitates with antibody to phosphotyrosine revealed a species migrating at approximately 130–140 kD that was specifically observed in Abl-transformed fibroblasts. This species may represent SMP phosphorylated by Abl, as SMP possesses a good match to SH2 binding domain recognized by Abl. The larger apparent molecular weight as compared with hSMP deduced molecular weight may reflect glycosylation or may be a result of its phosphorylated state.

SMP dimerizes with other important cellular regulatory proteins. To assay whether SMP dimerizes with other cellular proteins, the interaction trap/two hybrid analysis system was used. Briefly, a LexA-fusion and an epitope-tagged, activation-domain fusion to SMP were synthesized. The expression of proteins of the predicted size in yeast was confirmed using antibodies specific for the fusion moieties. Using a LexA-operator reporter, it was observed that LexA-SMP fusion protein activates transcription extremely weakly. However, LexA-SMP is able to interact with co-expressed activation domain-fused SMP to activate transcription of the reporter, indicating that it is able to form dimers (or higher order multimers).

SMP joins p130cas in defining a new family of docking adapters that, through multiple associations with signalling molecules via SH2 binding domains, is likely to coordinate changes in cellular growth regulation. The interactions between SMP homodimers and SMP-p130cas heterodimers may negatively regulate SMP and p130cas proteins by making them inaccessible to their targets. Alternatively, SMP and p130cas could work together to recruit new proteins to the signalling complex. The fact that the novel C-terminal domain shared between SMP and p130cas has the ability to cause pseudohyphal formation in yeast suggests that these proteins may directly alter cellular morphology by interacting with the cytoskeleton. In fact, previous yeast-morphology based screens for higher eucaryotic proteins have tended to isolate cytoskeletally related proteins. This invention therefore provides reagents influencing the changes in cell morphology that accompany oncoprotein-mediated transformation in carcinogenesis.

The present invention is not limited to the embodiments specifically described above, but is capable of variation and modification without departure from the scope of the appended claims.

What is claimed is:

1. An isolated human signal mediator protein between about 795 and about 875 amino acids in length, said protein being encoded by SEQ ID NO: 1 and comprising an amino-terminal SH3 domain, an internal domain that includes a multiplicity of SH2 binding motifs, said SH2 binding motifs being encoded by consensus nucleic acid sequences, and a carboxy-terminal effector domain, said carboxy-terminal effector domain, when produced in *Saccharomyces cerevisiae*, being capable of inducing pseudohyphal budding in said *Saccharomyces cerevisiae* under low nitrogen culture conditions.

2. The protein of claim 1, comprising the amino acid sequence of SEQ ID NO. 2.

3. An isolated polypeptide produced by expression of an isolated nucleic acid sequence selected from the group consisting of:

a) SEQ ID NO: 1;

b) a sequence specifically hybridizing with the full complementary strand of SEQ ID NO: 1 under hybridization conditions of 5X SSC at 42° C. and wash conditions of 1X SSC at 65° C. wherein said sequence encodes a signal mediator protein;

c) a sequence encoding the polypeptide of SEQ ID NO: 2; and d) a nucleic acid sequence encoding a carboxy terminal effector domain of a signal mediator protein comprising an amino acid sequence corresponding to amino acids 626–834 of SEQ ID NO: 2.

4. A carboxy-terminal effector protein domain, said effector domain comprising a sequence of amino acids 626–834 of SEQ ID NO: 2.

5. An isolated mouse signal mediator protein which is between about 795 and about 875 amino acids in length and is encoded by a nucleic acid that specifically hybridizes with SEQ ID NO: 1 under hybridization conditions of 5X SSC at 42° C. and wash conditions of 1X SSC at 65° C., said protein comprising an amino-terminal SH3 domain, an internal domain that includes a multiplicity of SH2 binding motifs, said SH2 binding motifs being encoded by consensus nucleic acid sequences, and a carboxy-terminal effector domain, said carboxy-terminal effector domain, when produced in *Saccharomyces cerevisiae*, being capable of inducing pseudohyphal budding in said *Saccharomyces cerevisiae* under low nitrogen conditions.

* * * * *